US006992222B2

(12) United States Patent
Reisinger et al.

(10) Patent No.: US 6,992,222 B2
(45) Date of Patent: Jan. 31, 2006

(54) PROCESS FOR THE PREPARATION OF QUATERNARY SALT PHENOLATE SOLUTIONS

(75) Inventors: Claus-Peter Reisinger, Wixom, MI (US); Sven Michael Hansen, Leverkusen (DE); Peter Fischer, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 448 days.

(21) Appl. No.: 10/320,011

(22) Filed: Dec. 16, 2002

(65) Prior Publication Data

US 2003/0139626 A1 Jul. 24, 2003

(30) Foreign Application Priority Data

Dec. 27, 2001 (DE) .............................. 101 64 144

(51) Int. Cl.
*C07C 211/00* (2006.01)

(52) U.S. Cl. ..................................................... 564/296

(58) Field of Classification Search ................ 564/240, 564/296
See application file for complete search history.

(56) References Cited

U.S. PATENT DOCUMENTS 5,030,757 A * 7/1991 Berris ........................ 564/296
5,756,843 A * 5/1998 Webb et al. ................ 564/240

FOREIGN PATENT DOCUMENTS

DE 198 58 967 7/2000
DE 199 61 520 6/2001

* cited by examiner

*Primary Examiner*—Paul A. Zucker
(74) *Attorney, Agent, or Firm*—Joseph C. Gil; James R. Franks; Aron Preis

(57) ABSTRACT

The preparation of quaternary salt phenolate solutions is disclosed. The preparation entails mixing an aqueous hydroxide-containing solution with an organic phase that contains phenol and quaternary salt, distilling off the water and precipitating and filtering off the resulting salt.

7 Claims, No Drawings

PROCESS FOR THE PREPARATION OF QUATERNARY SALT PHENOLATE SOLUTIONS

FIELD OF THE INVENTION

The invention relates to a process for the preparation of solutions and more particularly to a solution of a quaternary cation and an anion from a deprotonated hydroxy aromatic in an organic solvent.

SUMMARY OF THE INVENTION

The preparation of quaternary salt phenolate solutions is disclosed. The preparation entails mixing an aqueous hydroxide-containing solution with an organic phase that contains phenol and quaternary salt, distilling off the water and precipitating and filtering off the resulting salt.

BACKGROUND OF THE INVENTION

Salts of quaternary cations and anions, in particular quaternary salt phenolate solutions, prepared from deprotonated hydroxy aromatics may be utilized as bases, catalysts or a reaction component in a range of organic reactions. Because such salts are not available commercially and their educts are relatively costly, there exists a need for methods of, on the one hand, synthesising these salts and, on the other, of recovering them from reaction mixtures.

DE A 19858967 describes a process for the preparation of liquid formulations of tetrabutylammonium phenolate. Here, phenolic solutions of tetrabutylammonium bromide and sodium phenolate are combined, excess phenol is distilled off, and sodium bromide is filtered off.

The disadvantage of this process is, on the one hand, the necessity of preparing sodium phenolate and distilling off phenol, with concomitant energy consumption, and, on the other hand, the optional difficulty of separating the sodium bromide which arises, which may be a very finely crystalline precipitate. It is therefore desirable to devise a simpler process having a lower capital cost requirement. A further object relates to the recovery of quaternary cation phenolate salts from reaction mixtures. The process should therefore also offer the possibility of working up reaction mixtures such that the quaternary cation phenolate solutions are able to be recycled again.

DETAILED DESCRIPTION OF THE INVENTION

In working on this object, a reactive distillation process was found in which low-sodium quaternary salt phenolate solutions could surprisingly be obtained.

The present invention refers to a process for preparing an organic solution of a salt conforming to $(Q^{n+})_p[(^-O)_p-R]_n$ having water content of up to 2 wt. % comprising (i) contacting an aqueous solution of a hydroxide conforming to $M^{r+}(OH^-)_r$ with at least one quaternary salt conforming to $(Q^{n+})_m(Y^{m-})_n$, $R-(OH)_p$ and at least one solvent which is not completely miscible with water to form a mixture, (ii) partially distilling the mixture to remove the water and precipitate the salt, and (iii) separating the precipitated salt, wherein $Q^{n+}$ is a hexaalkylguanidinium ion or $(XR_o^+)_n$, wherein X denotes an atom of Group Va or VIa, o denotes an integer of 1 to 4, n denotes a natural number of 1 to 10, and R denotes at least one member selected from the group consisting of $C_1-C_{18}$-alkyl, $C_1-C_{18}$-cycloalkyl, $C_7-C_{18}$-aralkyl and $C_6-C_{18}$-aryl, with the proviso that two radicals R may be replaced by a ring, and $Y^{m-}$ is one or more members selected from the group consisting halide, nitrate, sulfate, hydrogen sulfate, carbonate, hydrogen carbonate, phosphate, hydrogen phosphate, dihydrogen phosphate, tetrafluoroborate, perchlorate, carboxylate and hexfluorophosphates, m denoted an integer of 1 to 3, and where in $R-(OH)_p$, R denotes an aromatic radical and p is an integer of 0 to 4, said solvent has a boiling point of 40 to 200° C., and $M^{r+}(OH^-)_r$ is at least one hydroxide of the elements selected from Groups Ia and Ia of the Periodic Table and r is 1 or 2.

The water content is preferably up to 0.5 wt. % and particularly preferably up to 0.2 wt. %.

The present invention also provides a process for the recovery of quaternary salts from reaction mixtures and the recycling thereof into the reactions as organic solutions of mixtures of salts $(Q^{n+})_p[(^-O)_p-R]_n$ and $(Q^{n+})_m(Y^{m-})_n$, characterised in that mixtures comprising, inter alia, 1. one or more quaternary salts $(Q^{n+})_m(Y^{m-})_n$ and
2. a hydroxy aromatic $R-(OH)_p$ as well as optionally
3. one or more organic solvents are reacted in the following manner:

a) an aqueous solution of a hydroxide $M^{r+}(OH^-)_r$, as well as the organic solution which comprises quaternary salts $(Q^{n+})_m(Y^{m-})_n$ and $R-(OH)_p$ are contacted, water is then removed by partial distillation of the mixture, and a precipitated salt is finally separated, wherein an organic solution which comprises $(Q^{n+})_p[(^-O)_p-R]_n$ and/or $(Q^{n+})_m(Y^{m-})_n$ and/or $R-(OH)_p$ is obtained, b) the $(Q^{n+})_p[(^-O)_p-R]_n$ which is comprised in this organic solution is returned into the reaction following optional further working-up steps.

In the quaternary salts which are utilized within the framework of the present invention, the relevant quaternary cation $Q^{n+}$ is typically constituted by compounds corresponding to the formula $(XR_o^+)_n$, wherein X stands for a Group Va or VIa atom, o stands for an integer between 0 and 4, and R stands for $C_6$- to $C_{18}$-aryl, $C_7$- to $C_{18}$-aralkyl or $C_1$- to $C_{20}$-alkyl radicals, independently of one another.

These are generally constituted here by, for example, ammonium salts, guanidinium salts, phosphonium salts or sulfonium salts, optionally also mixtures thereof, substituted with organic radicals. The letter n stands for a natural number. Oligomers having n>1 ((n−1) R radicals then bridge between two Xs) may also be utilized, however monomeric ions (n=1) are preferred.

Ammonium ions, guanidinium ions, phosphonium ions, sulfonium ions and sulfoxonium ions which have as the organic radicals $C_6$- to $C_{18}$-aryl, $C_7$- to $C_{18}$-aralkyl or $C_1$- to $C_{20}$-alkyl radicals are suitable for use in the process according to the invention. The radicals may in each case all be identical or may be different and may themselves be substituted. Two substituent radicals may in each case be replaced by a ring, mixtures of a plurality of quaternary cations may optionally also be utilized.

The following ions might be listed as examples: tetramethylammonium, tetra-n-ethylammonium, tetra-n-propylammonium, tetra-n-butylammonium, di-n-decyldimethylammonium, di-n-octadecyldimethylammonium, tri-n-decylmethylammonium, N-methyl-N-decylmorpholinium, N-methyl-N-ethylpyrrolidinium, N-(2-hydroxyethyl)-N-ethylpiperidinium, benzyltributylammonium, phenyltrimethylammonium, tetraphenylammonium, tetramethylphosphonium, tetra-n-ethylphosphonium, tetra-n-propylphosphonium, tetra-n-butylphosphonium, di-n-decyldimethylphosphonium, di-n-octadecyldimethylphosphonium, tri-n-decylmethylphosphonium, benzyltributylphosphonium, phenyltrimethylphosphonium, tetraphenylphosphonium, hexaethylguanidinium, tetramethylbishexylguanidinium.

Tetraalkylammonium ions, tetraphenylammonium ions, tetraalkylphosphonium ions, tetraphenylphosphonium ions and hexaalkylguanidinium ions are preferably utilized. Tetrabutylammonium ions, tetrabutylphosphonium ions or tetraphenylphosphonium ions are particularly preferably utilized.

Halides, nitrates, sulfates, hydrogen sulfates, carbonates, hydrogen carbonates, phosphates, hydrogen phosphates, dihydrogen phosphates, tetrafluoroborates, perchlorates, carboxylates or hexafluorophosphates may, for example, be utilized as counter-anions $Y^{m-}$ to the quaternary cations. The letter m stands for a natural number. Mixtures of different anions are possible. Halides are preferred, particularly preferably bromide.

Hexaalkylguanidinium halides, tetraalkylammonium halides and tetraarylphosphonium halides are preferred, particularly preferably tetrabutylammonium bromide, tetrabutylammonium chloride, tetraphenylphosphonium bromide and tetrabutylphosphonium bromide.

The quantity of such a quaternary salt may be, for example, from 0.01 to 30 wt. %, in relation to the weight of the reaction mixture. This quantity is preferably from 0.5 to 15 wt. %, particularly preferably 1 to 5 wt. %.

The aromatic hydroxy compounds R—(OH)$_p$ which are reactable according to the invention and in which R stands for an aromatic radical and p stands for an integer from 0 to 4 are preferably selected from the group comprising monohydroxylated aromatic compounds (p=1), dihydroxylated aromatic compounds (p=2) or polyhydroxylated aromatic compounds (p<=4) or bisphenols (p=2), which may have from 0 to 4 substituents in the sense of $C_1$–$C_{18}$-alkyl or -cycloalkyl, $C_6$–$C_{18}$-aryl, $C_7$–$C_{18}$-aralkyl, $C_1$–$C_{18}$-alkoxy, fluorine, chlorine or bromine. The alkyl, aryl and aralkyl substituents may themselves also be substituted or may carry functional groups such as ether groups, thioether groups, keto groups, epoxy groups, halogens, heterocyclic rings. Aromatic substituent rings may be annelated or bridged, a plurality of radicals may be bonded to form cycles.

Examples are monohydroxy compounds such as phenol, o-, m- or p-cresol, o-, m-or p-chlorophenol, o-, m- or p-ethylphenol, o-, m- or p-propylphenol, o-, m- or p-tert.-butylphenol, o-, m- or p-isooctylphenol, o-, m- or p-stearylphenol, o-, m- or p-phenylphenol, o-, m- or p-cyclohexylphenol, o-, m- or p-methoxyphenol, 2,6-dimethylphenol, 2,4-dimethylphenol, 3,4-dimethylphenol, 1-naphthol, 2-naphthol or di- or polyhydroxy compounds such as resorcinol and hydroquinone, as well as bisphenols such as 2,2-bis(4-hydroxyphenyl)propane (bisphenol A), 2,2-bis(3,5-dimethyl-4-hydroxyphenyl)propane, 1,1-bis(4-hydroxyphenyl)cyclohexane, 1,1-bis(4-hydroxyphenyl)-3,3,5-trimethylcyclohexane (bisphenol TMC), α,α-bis(4-hydroxyphenyl)-m-diisopropylbenzene, 6,6'-dihydroxy-3,3,3',3'-tetramethyl-1,1'-spiro-(bis)indane, 4,4'-dihydroxybiphenyl, or 2,4'-dihydroxybiphenyl.

Mixtures of different aromatic hydroxy compounds may also be utilized. Monohydroxy compounds are preferably utilized, particularly preferably phenol.

Single substances or substance mixtures, which are only partially miscible with water and are inert to the substances used are utilized as the organic solvent. Solvents having a boiling point between approximately 40 and 200° C. are preferred, particularly preferably solvents having a boiling point between approximately 100 and 160° C. Solvents which form azeotropic mixtures with water are furthermore preferred. The inert solvent may be comprised in the mixture at a content of from 1 to 99 wt. %, preferably 20 to 98 wt. %, particularly preferably 40 to 98 wt. %, in relation to R—(OH)$_p$.

Hydrocarbons, halogenated hydrocarbons and aromatic solvents such as chlorobenzene, dichlorobenzene, fluorobenzene, benzene, toluene, the xylenes, anisole, cyclohexane, petroleum ether, methylene chloride, chloroform or 1,2-dichloroethane, dipolar aprotic solvents such as dimethyl acetamide, acetonitrile, N-methylpyrrolidone, esters, ethers such as dioxane, tetrahydrofuran, tert.-butylmethyl ether and etherified glycols may, for example, be utilized as the solvent, particularly preferably chlorobenzene.

Embodiments which make use of the parameters, compounds, definitions and explanations named as being preferred, particularly preferred or most particularly preferred are preferred, particularly preferred or most particularly preferred.

The aforementioned general definitions, parameters, compounds and explanations or those mentioned in areas of preference may, however, also be combined at will with one another, that is to say between the areas and the areas of preference in each case.

$M^{r+}(OH^-)_r$ stands for one or more hydroxides from groups Ia (r=1) or IIa (r=2) of the Periodic Table. Examples are lithium hydroxide, sodium hydroxide, potassium hydroxide, calcium hydroxide. Potassium hydroxide, sodium hydroxide and calcium hydroxide are preferred, particularly preferably sodium hydroxide. $M^{r+}(OH^-)_r$ may be dispensed as an aqueous solution or a suspension into the reaction mixture, it may alternatively be added as a solid together with water, wherein the former is preferred. The most highly concentrated possible solution of $M^{r+}(OH^-)_r$ is preferably utilized.

A process is preferred in which the aqueous phase has a pH greater than approximately 9, particularly preferably greater than approximately 11, most particularly preferably greater than approximately 12.5, before the reactive distillation is carried out.

Depending on the demands made of the organic solutions, $(Q^{n+})_m(Y^{m-})_n$ may be approximately 1 to 99.9% converted to $(Q^{n+})_p[(^-O)p$-$R]_n$. This may be positively desirable, for example if in a subsequent reaction $(Q^{n+})_m(Y^{m-})_n$ functions as a phase transfer catalyst or conducting salt. The present invention therefore also provides organic solutions which comprise both $(Q^{n+})_p[(^-O)_p$—$R]_n$ and $(Q^{n+})_m(Y^{m-})_n$.

The ratio of hydroxide $M^{r+}(OH^-)_r/(Q^{n+})_m(Y^{m-})_n$ may, depending on the desired ratio of $(Q^{n+})_p[(^-O)_p$—$R]_n$ and $(Q^{n+})_m(Y^{m-})_n$ in the organic phase, be approximately 0.05 [m/r] to 1.2 [m/r]. If the ratio is increased the quantity of $(Q^{n+})_p[(^-O)_p$—$R]_n$ formed increases, provided an excess of R—(OH)$_p$ is available. For virtually complete conversion a ratio of approximately 1 [m/r] may be sufficient. Higher ratios then lead to a generally undesirable higher $M^{r+}$ content of the organic solution.

The molar ratio [R—(OH)$_p$]/[$M^{r+}(OH^-)_r$] between R—(OH)$_p$ and the hydroxide $M^{r+}(OH^-)_r$ should initially be equal to or greater than 1 [r/p], preferably greater than approximately 1.1 [r/p], particularly preferably greater than approximately 3.1 [r/p].

In the reactive distillation a precipitate forms which in most cases consists of $(M^{r+})_m(Y^{m-})_r$ but which may also comprise other metals which the reaction mixture comprises or species generated by deprotonation of $Y^{m-}$. This precipitate may be separated from the organic solution by methods for the separation of liquids from solids, which are known to those skilled in the art, such as filtration, suction filtration, decanting, sedimentation, centrifuging, and the like. Because it becomes concentrated as a sediment in the bottom of the distillation apparatus, it may be removed there in batch-wise or continuous manner. For example, a side stream which is removed at the base of the distillation apparatusmay suspend the salt. The stream is then guided by way of a filter and is returned, free of solids, into the column.

High $M^{r+}$ contents of organic solutions may be disruptive in industrial processes because the salts which comprise $M^{r+}$ are generally poorly soluble in organic solution and may undergo uncontrolled precipitation in the reactors, possibly giving rise to blockages and similar problems.

It has surprisingly been found that the $M^{r+}$ content of the solutions prepared by the process according to the invention is less than approximately 50 mg/kg. Solutions which have an $M^{r+}$ content of less than approximately 10 mg/kg are preferred, particularly preferably organic solutions having an $M^{r+}$ content of less than approximately 5 mg/kg.

Organic solutions prepared from $(Q^{n+})_p[(^-O)_p-R]_n$ and $(Q^{n+})_m(Y^{m-})_n$ are, for example, necessary in the direct carbonylation of phenol with carbon monoxide and oxygen to diphenyl carbonate. The present invention therefore provides the use of the organic solutions according to the invention in oxidative carbonylation reactions.

In the process according to the invention for the working-up and recycling of organic solutions of salts $(Q^{n+})_p[(^-O)_p-R]_n$ and $(Q^{n+})_m(Y^{m-})_n$ the commercial availability of, for example, tetrabutylammonium bromide $\{(Q^{n+})_m(Y^{m-})_n\}$ may be put to use for the synthesis of the tetrabutylammonium phenolate $(Q^{n+})_p[(^-O)p-R]_n$. In the oxidative direct carbonylation of phenol, for example, this tetrabutylammonium phenolate is utilized as a phenolate base, and tetrabutylammonium bromide is in addition also utilized. The protonation of phenolate to phenol, which is brought about during the reaction by the carbon dioxide by-product and water, and hence the consumption of $(Q^{n+})_p[(^-O)_p-R]_n$, for example, or the possibility of a partial or complete protonation taking place during working-up steps, make regeneration of this phenolate base an important object of this process. The process according to the invention enables a stream which arises during working-up and which generally comprises unreacted phenol $(R-(OH)_p)$, a quaternary bromide $((Q^{n+})_m(Y^{m-})_n)$ and a solvent, alongside other components, to be converted completely or partially to the quaternary phenolate.

The process may be carried out such that the stream is divided and only a part stream is reacted completely or partially in order to regenerate the base. Alternatively, the entire stream may also be reacted with a quantity of $M_{r+}(OH^-)_r$ such as is necessary for the desired quantity of phenolate. Since it has surprisingly been found that precisely in the case of substoichiometric conditions, that is to say when ratios of $M^{r+}(OH^-)_r/(Q^{n+})_m(Y^{m-})_n$ are less than 1 [m/r], conversion is virtually quantitative with the quantity of $M^{r+}(OH^-)_r$, the desired quantity of quaternary salt phenolatemay be adjusted with relative ease. The processmay be managed such that in the reaction feed only $(Q^{n+})_m(Y^{m-})_n$ is dispensed in order to compensate for losses, and the $(Q^{n+})_p[(^-O)_p-R]_n$ losses are made up in their entirety by a reaction according to the invention.

Following the reactive distillation the organic solutions obtained still comprise a certain residual moisture. If they are to be used in reactions in which water has a highly disruptive effect, it may be necessary to dry them still further before further use. In this case, processes known to those skilled in the art, such as, for example, drying over anhydrous salts, stripping-out, molecular sieves, azeotropic distillation, may be employed. Other types of working-up, such as, for example, concentrating the solvent more highly, separating R—(OH)p, removing the residual metal content, for example by ion exchange or precipitation, evaporation, precipitation or recrystallisation of the $(Q^{n+})_p[(^-O)_p-R]_n$ salts, may likewise take place before recycling into the reaction.

A precipitate which comprises the unreacted part of the $Y^{m-}$ arises in the reactive distillation. If this is a valuable anion such as, for example, $PF_6^-$ or even bromide, it may be worthwhile to work up this anion also, for example by ion exchange, conversion to volatile species followed by distillation, recrystallisation of the precipitate or other methods.

Furthermore, metal salts such as may be present as catalyst components in the reaction mixture may likewise be precipitated and separated in this reactive distillation, enabling them to be worked up in worthwhile manner for ecological or economic reasons. A number of metal ions precipitate as hydroxides under the reaction conditions. Precipitations with $Y^{m-}$ or, if these anions are derived from polybasic acids, with the $Y'^{(m+1)-}$ or $Y''^{(m+2)-}$ (for example $Y^{m-}$=dihydrogen phosphate, m=1, $Y'^{(m+1)-}$=hydrogen phosphate, $Y''^{(m+2)-}$=phosphate) which are generated from them by deprotonation, are also possible and are utilized optionally for the separation of metals.

The ratios of organic to aqueous $M^{r+}(OH^-)_r$ phase and hence, by way of the necessary stoichiometry, the concentration of the $M^{r+}(OH^-)_r$ phase, should be selected so as to be as high as possible in order to avoid incurring unnecessary distillation costs for removal of the water. The utilization of excessively concentrated solutionsmay, on the other hand, lead to precipitation of $M^{r+}(OH^-)_r$, which is generally undesirable because it slows the reaction markedly. Mass ratios of organic to aqueous phase of from approximately 5:1 to approximately 200:1, particularly preferably approximately 10:1 to 150:1, are therefore preferred.

The ratio utilized of hydroxide $M^{r+}(OH^-)_r/(Q^{n+})_m(Y^{m-})_n$ may, depending on the desired ratio of $(Q^{n+})_p[(^-O)_p-R]_n$ and $(Q^{n+})_m(Y^{m-})_n$ in the organic phase, be from approximately 0.01 [m/r] to 1.2 [m/r]. If the ratio is increased, the quantity of $(Q^{n+})_p[(^-O)_p-R]_n$ which is formed increases, provided an adequate quantity of $R-(OH)_p$ is present. For virtually complete conversion a ratio of approximately 1 [m/r] may be sufficient. Ratios of $M^{r+}(OH^-)_r/(Q^{n+})_m(Y^{m-})_n$ of from approximately 0.1 [m/r] to 1.1 [m/r] are therefore preferred. Higher ratios then lead to a generally undesirable higher $M^{r+}$ content of the organic solution and to a high $R-(OH)_p$ loss.

The process requires the presence of $R-(OH)_p$ for formation of the product; $R-(OH)_p$ in excess surprisingly facilitates the preparation of the solutions. Although the process may be utilized in a multitude of reactions, reactions in which $R-(OH)_p$ is used as an educt are preferred. Reactions in which the reaction product is an organic ester, for example an ester of $R-(OH)_p$, are furthermore preferred. Esters of carbonic acid with $R-(OH)_p$, for example diphenyl carbonate, are particularly preferred.

It has surprisingly been found in respect of the working-up process according to the invention that the $M^{r+}$ content of the solutions prepared by the process according to the invention is less than approximately 20 mg/kg. Solutions which have an $M^{r+}$ content of less than approximately 10 mg/kg are preferred, particularly preferably organic solutions having an $M^{r+}$ content of less than approximately 5 mg/kg.

Thirdly, the present invention provides a process for the selective preparation of organic solutions of salts $(Q^{n+})_p[(^-O)_p—R]_n$ and $(Q^{n+})_m(Y(1)^{m-})_n$, since it has surprisingly been found that in a mixture of two quaternary salts $(Q^{n+})_m(Y(1)^{m-})_n$ and $(Q^{n+})_s(Y(2)^{s-})_n$, $(Q^{n+})_s(Y(2)^{s-})_n$ may be reacted highly selectively with the hydroxide $M^{r+}(OH^-)_r$.

The present invention therefore also provides a process for the preparation of organic solutions of salts $(Q^{n+})_p[(^-O)_p—R]_n$ and $(Q^{n+})_m(Y(1)^{m-})_n$, from a quaternary cation $(Q^{n+})$ and a hydroxy aromatic $(R—(OH)_p)$, characterised in that an aqueous solution of a hydroxide $M^{r+}(OH^-)_r$ is contacted in intimate manner with at least two different quaternary salts $(Q^{n+})_m(Y(1)^{m-})_n$ and $(Q^{n+})_s(Y(2)^{s-})_n$ and at least one solvent which is not completely miscible with water, and the water is removed by partial distillation of the mixture, and a precipitated salt is finally separated, wherein a low-water to water-free organic solution is obtained which comprises $(Q^{n+})_p[(^-O)_p—R]_n$ and/or $(Q^{n+})_m(Y(1)^{m-})_n$ and/or $R—(OH)_p$.

Depending on the selected stoichiometry of the compounds, organic solutionsmay be prepared which comprise $(Q^{n+})_p[(^-O)_p—R]_n$, $(Q^{n+})_m(Y(1)^{m-})_n$ and $(Q^{n+})_s(Y(2)^{s-})_n$, wherein the molar ratio $(Q^{n+})_m(Y(1)^{m-})_n/(Q^{n+})_s(Y(2)^{s-})_n$ may increased markedly by comparison with the starting ratio.

It is a further option to prepare solutions which have virtually no $(Q^{n+})_s(Y(2)^{s-})_n$ and are composed only of the quaternary salts $(Q^{n+})_p[(^-O)_p—R]_n$ and $(Q^{n+})_m(Y(1)^{m-})_n$. In this case virtually the complete quantity of $(Q^{n+})_m(Y(1)^{m-})_n$, which was utilized may remain unreacted in the organic solution or a part of the $(Q^{n+})_m(Y(1)^{m-})_n$ may likewise be converted with $M^{r+}(OH^-)_r$ to $(Q^{n+})_p[(^-O)_p—R]_n$.

$(Q^{n+})_m(Y(1)^{m-})_n$ and $(Q^{n+})_s(Y(2)^{s-})_n$ are in this case two different elements of the quantity of those compounds which are defined by $(Q^{n+})_m(Y^{m-})_n$, wherein m, n and s are natural numbers which may be the same or different. Preferably, m is less than s. Halide (X—) & sulfate $(SO_4^{2-})$, particularly preferably bromide $(Br^-)$ & sulfate, are a preferred combination $Y(1)^{m-}$ & $Y(2)^{s-}$. Bromide & chloride are furthermore particularly preferred.

The process for the selective preparation of quaternary salt phenolate may also be employed advantageously in the working-up of reaction mixtures. In reactions which, for example, require an organically soluble bromide source and a phenolate base, it is possible to compensate for the phenolate loss by the process according to the invention. In this case bromide, which is costly, need not absolutely be utilized as the educt, as a sulfate or chloridemay also be dispensed in addition and converted in selective manner to the phenolate, without resultant loss of a significant proportion of the bromide source.

The distillations according to the invention may be carried out in one step, in a plurality of steps or in continuous manner. Continuous distillation is generally preferred.

The processes according to the invention for the preparation and working-up are carried out at a temperature of from −10 to 200° C., preferably 10 to 130° C., particularly preferably 20 to 90° C., and at a pressure of from 0.001 to 20 bar, preferably 0.005 to 10 bar, particularly preferably 0.01 to 5 bar.

It is likewise known to those skilled in the art that the process is dependent on the chemical nature of the species $R—(OH)_p$, $(Q^{n+})_m(Y^{m-})_n$ and the solvent S and that, depending on the boiling characteristics of the $R—(OH)_p$/water mixture and the desired water and solvent depletion and separation efficiency, the distillation must have the number of theoretical separation stages which is suitable for the specific separation problem and a contact time adapted to the kinetics of the reactive distillation.

EXAMPLES

After the distillation has been performed and the solid has been filtered off, the solution is examined by gas chromatography to determine the concentration of the components. Tetrabutylammonium bromide $(TBAB,=(Q^{n+})_m(Y^{m-})_n)$ here decomposes into tributylamine and butyl bromide, which are detected. The ratio of tetrabutylammonium phenolate $(TBAP,=(Q^{n+})_p[(^-O)_p—R]_n)$ to tetrabutylammonium bromidemay be calculated from the ratio of tributylamine to butyl bromide.

Example 1

4.52 g of a 25% sodium hydroxide solution are added to 18.27 g tetrabutylammonium bromide, 66 g phenol and 315 g chlorobenzene. A mixture of water and chlorobenzene is distilled off under vacuum (approximately 350 to 200 mbar) at a bottom temperature of 80° C. After approximately 140 g have been distilled off, the precipitate is filtered off, washed with methylene chloride and dried. 2.96 g are obtained of a white solid which is shown by elemental analysis to comprise 72% bromine.

The filtrate has a water content of 0.07% (Karl Fischer titration) and a sodium content of 4.5 mg/kg. The composition of the quaternary salts is shown by GC to be approximately 41 wt. % tetrabutylammonium bromide and 59 wt. % tetrabutylammonium phenolate.

Example 2

4.54 g of a 50% sodium hydroxide solution are added to 18.27 g tetrabutylammonium bromide, 66 g phenol and 315 g chlorobenzene. A mixture of water and chlorobenzene is distilled off under vacuum (approximately 70 mbar) at a bottom temperature of 60° C. After approximately 300 g have been distilled off, the precipitate is filtered off, washed with methylene chloride and dried. 5.83 g of a white solid are obtained.

The filtrate has a water content of 0.07% (Karl Fischer titration) and a sodium content of 470 mg/kg. The composition of the quaternary salts is shown by GC to be approximately 10 wt. % tetrabutylammonium bromide and 90 wt. % tetrabutylammonium phenolate.

Example 3

2.26 g of a 50% sodium hydroxide solution are added to 9.14 g tetrabutylammonium bromide, 8.2 g tetrabutylammonium sulfate, 66 g phenol and 315 g chlorobenzene. A mixture of water and chlorobenzene is distilled off under vacuum (approximately 130 mbar) at a bottom temperature of 70° C. After approximately 140 g have been distilled off, the precipitate is filtered off, washed with methylene chloride and dried. 2.15 g are obtained of a white solid which is shown by elemental analysis to comprise 3.0% bromine.

The filtrate has a sodium content of 29 mg/kg. The composition of the quaternary salts is shown by GC to be 40 wt. % tetrabutylammonium bromide and 60 wt. % tetrabutylammonium phenolate.

Example 4

7.38 g of a 43.1% potassium hydroxide solution are added to 18.27 g tetrabutylammonium bromide, 66 g phenol and 315 g chlorobenzene. A mixture of water and chlorobenzene is distilled off under vacuum (approximately 60 mbar) at a bottom temperature of 55° C. After approximately 330 g have been distilled off, the precipitate is filtered off, washed with methylene chloride and dried. 6.74 g are obtained of a white solid which is shown by elemental analysis to comprise 67.1% bromine.

The filtrate has a potassium content of 1700 mg/kg. The composition is shown by GC to be 0.7 wt. % tetrabutylammonium bromide and 99.3 wt. % tetrabutylammonium phenolate.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for the recovery of quaternary salts from a reaction mixture that contains one or more quaternary salts $((Q^{n+})_m(Y^{m-})_n)$ and a hydroxy aromatic $R-(OH)_p$ and an optional organic solvent, said process comprising:
    a) mixing an aqueous solution of a hydroxide $M^r(OH^-)_r$, an organic solution that contains quaternary salt $(Q^{n+})_m(Y^{m-})_n$ and $R-(OH)_p$ to form a mixture;
    b) removing the water by partial distillation of the mixture;
    c) separating a salt by precipitation to obtain an organic solution that contains at least one of $(Q^{n+})_p[(^-O)_p-R]_n$, $(Q^{n+})_m(Y^{m-})_n$ and $R-(OH)_p$; and
    d) recycling the $(Q^{n+})_p[(^-O)_p-R]_n$ included in the organic solution into a reaction for the preparation of a diaryl carbonate, wherein, $Q^{n+}$ is selected from the group consisting of hexaalkylguanidinium ion and $(XR'_o{}^+)_n$, wherein X denotes an atom of Group Va or VIa, o denotes an integer of 1 to 4, n denotes a natural number of 1 to 10, and R' denotes at least one member selected from the group consisting of $C_1-C_{18}$-alkyl, $C_1-C_{18}$-cycloalkyl, $C_7-C_{18}$-aralkyl and $C_6-C_{18}$-aryl, with the proviso that two radicals R' may be replaced by a ring, $Y^{m-}$ is selected from the group consisting halide, nitrate, sulfate, hydrogen sulfate, carbonate, hydrogen carbonate, phosphate, hydrogen phosphate, dihydrogen phosphate, tetrafluoroborate, perchlorate, carboxylate, hexfluorophosphates and combinations thereof, and m is an integer of 1 to 3, with $R-(OH)_p$ and $R-(O)-_p$, R denotes an aromatic radical and p is an integer of 0 to 4, and $M^{r+}(OH^-)_r$ is at least one hydroxide of the elements selected from Groups Ia and IIa of the Periodic Table, and r is 1 or 2.

2. The process of claim 1 wherein the molar ratio of $M^r(OH^-)_r$ to $(Q^{n+})_m(Y^{m-})_n$ is 0.05 to 1.2.

3. The process of claim 1 wherein the organic solution has an $M^{r+}$ content of less than 50 mg/kg.

4. The process of claim 1 wherein $Q^{n+}$ represents at least one member selected from the group consisting of tetrabutylammonium, tetraphenylammonium, tetrabutylphosphonium, tetraphenylphosphonium and hexaalkylguanidinium.

5. The process of claim 1 wherein $Y^{m-}$ represents a chloride or bromide.

6. The process of claim 1 wherein $R-(OH)_p$ is at least one member selected from the group consisting of phenol, cresol, chlorophenol, alkylphenol, methoxyphenol, dimethylphenol, naphthol, resorcinol, hydroquinone, 2,2-bis(4-hydroxyphenyl)propane, 2,2-bis(3,5-dimethyl-4-hydroxyphenyl)propane, 1,1-bis(4-hydroxyphenyl)cyclohexane, 1,1-bis(4-hydroxyphenyl)-3,3,5-trimethylcyclohexane, α,α-bis(4-hydroxyphenyl)-m-diisopropylbenzene, 4,4'-dihydroxybiphenyl, 2,4'-dihydroxybiphenyl and 6,6'-dihydroxy-3,3,3',3'-tetramethyl-1,1'-spiro-(bis)indane.

7. The process of claim 1 wherein the solvent forms an azeotrope with water.

* * * * *